United States Patent
Bauer et al.

[11] Patent Number: 5,912,359
[45] Date of Patent: Jun. 15, 1999

[54] DIMALEINIMIDO-SUBSTITUTED DIHYDROXYALKANES WHICH CAN BE USED AS CROSSLINKING REAGENTS AND PROCESS FOR THEIR PREPARATION

[75] Inventors: Paul J. Bauer, Jülich; Volker Hagen, Berlin, both of Germany

[73] Assignees: Forschungszentrum Jülich GmbH, Jülich; Forschungsverbund Berlin E.V., Berlin, both of Germany

[21] Appl. No.: 09/043,263

[22] PCT Filed: Sep. 11, 1996

[86] PCT No.: PCT/DE96/01742

§ 371 Date: Aug. 27, 1998

§ 102(e) Date: Aug. 27, 1998

[87] PCT Pub. No.: WO97/10209

PCT Pub. Date: Mar. 20, 1997

[30] Foreign Application Priority Data

Sep. 13, 1995 [DE] Germany .......................... 195 33 867

[51] Int. Cl.⁶ .................. C07D 207/404; C07D 207/408; C07D 207/452; C07K 1/10

[52] U.S. Cl. .......................... 548/546; 548/547; 548/548; 530/350

[58] Field of Search .................................. 548/546, 548, 548/547; 530/350

[56] References Cited

U.S. PATENT DOCUMENTS 2,444,536  7/1948  Searle ...................................... 260/313

FOREIGN PATENT DOCUMENTS 4014540  11/1991  Germany .

OTHER PUBLICATIONS

Feit et al., Alkylating Agents Related to 2.2'–biaziridine, J. Med. Chem. 10(4) 697–700, Dec. 1967.

Srinivaschar, K. et al, "New Protein Cross–linking Reagents That Are Cleaved by Mild Acid", Biochem. 28, pp. 2501–2509 (1989).

Feit, P. W. et al, "Alkylating Agents Related to 2,2'–Biaziridine,. I. Compounds Derived from 1,4–Diamino–2,3–butanediol", J. Med Chem. 10, pp. 697–700 (1967).

Moore, J. E., et al, *J. Am. Chem. Soc.* 78:2414–2418 (1956).

Kovacic, P., et al, *J. Am. Chem. Soc.* 81:1187–1190 (1959.

Sato, S., et al, *J. Biochem.* 90:1177–1185 (1981).

Chantler, P. D., et al, *J. Biological Chem.* 263:938–944 (1988).

*Primary Examiner*—Johann Richter
*Assistant Examiner*—Dominic Keating

[57] ABSTRACT

The invention relates to novel dimaleinimido-substituted dihydroxyalkanes, to a process for their preparation as well as to their use as cross-linking reagents, e.g. in analytical methods. A disadvantage of the cleavable bismaleinimido derivatives used so far, which react with SH groups, is that the subsequent cleavage of the cross-linking reagents from the proteins must take place in acidic or alkaline media. The objective of the invention is to prepare novel cleavable cross-linking reagents which react with SH groups or proteins and which form cross-links which can be cleaved under mild conditions not requiring strongly acidic or basic media. This objective is sought through the preparation and use of dimaleinimido-substituted dihydroxyalkanes having the general formula I

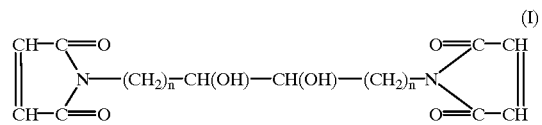

where n=1 to 6, preferably 1 or 2.

12 Claims, 1 Drawing Sheet

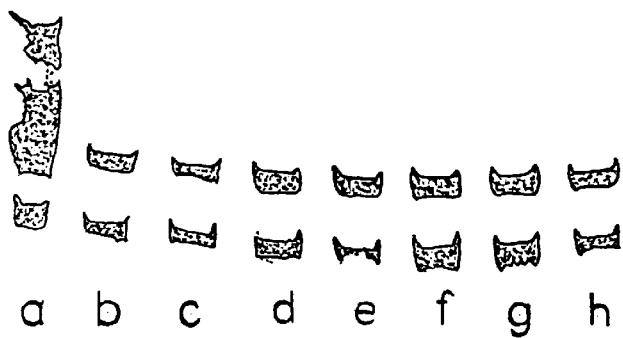
a b c d e f g h
Fig.1.
Fig.2.
1ˢᵗ Dimension, Immunoblot Analysis
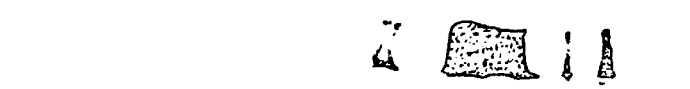

DIMALEINIMIDO-SUBSTITUTED DIHYDROXYALKANES WHICH CAN BE USED AS CROSSLINKING REAGENTS AND PROCESS FOR THEIR PREPARATION

This application is a 371 of PCT/DE96/01742 filed Sep. 11, 1996.

FIELD OF THE INVENTION

This invention relates to dimaleinimido-substituted compounds, to a process for their preparation, to their use as cross-linking reagents, to the preparation of cross-linked proteins therefrom, to a method for decreasing the molecular weight of proteins thus-cross-linked by means of a cleavage reaction, and to methods, including analytical methods, for lowering the solubility of proteins or for making them more easily removable from an environment or a medium such as a cell or a solution, through cross-linking, and subsequently recovering or restoring the non-cross-linked protein from the cross-linked protein thus removed or insolubilized, so that the restored or recovered protein can be detected or isolated or more accurately characterized.

DESCRIPTION OF THE PRIOR ART

In the realm of protein research, widespread use is made especially of bifunctional cross-linking reagents ("cross-linkers"). These are substances which have two functional groups which are either identical (homobifunctional cross-linking reagents) or else different (heterobifunctional cross-linking reagents). The functional groups react with the corresponding reactive amino acid lateral chains of proteins, thus forming bridges between the side chains. The bridge formation can take place either on the intramolecular level and thus be employed, for instance, to determine distances between two adjacent reactive groups in the protein such as, for example, in the active center of enzymes, or else the bridge formation takes place on the intermolecular level between two or more protein molecules, so that higher molecular complexes are formed. Such intermolecular cross-linking reagents can be employed, for instance, to analyze antigen-antibody interactions, the structure of multi-enzyme complexes, the arrangement of proteins in membranes and many other biological environments. In addition to non-cleavable bifunctional cross-linking reagents, there is also widespread use of cleavable cross-linking reagents.

Proteins (and polypeptide chains in general) can be cross-linked in variety of ways. Some proteins have free sulfhydryl (—SH) groups (also called thiol or mercapto groups) available on the polypeptide chains, and these groups are reactive toward various cross-linking agents. Mercaptalbumin, for example, has a single reactive thiol group on each molecule, hence cross-linking of mercaptalbumin results in the formation of a "dimer". See Cross-linking reagents which are reactive with respect to SH groups include, among others, bismaleinimido-substituted aliphatic or aromatic compounds such as, for example, the uncleavable compounds dimaleinimidohexane (M. D. Partis et al. (1983), J. Prot. Chem. 2, 263), 4,4'-dimaleinimidostilbene (P. Chantler, S. M. Bower (1988), J. Biol. Chem. 263, 938) and p-phenylenedimaleinimide (J. E. Moore, W. H. Ward (1956), J. Am. Chem. Soc. 78, 2414), maleinimidomethyl-3-maleinimido-propionate that can be cleaved by bases (S. Sato, M. Nakao (1981), J. Biochem. 90, 1177) and several bis(maleinimidoalkoxy)-compounds that can be cleaved with acids (K. Srinivasachar, D. M. Jr. Neville (1989), Biochemistry 28, 2501).

A disadvantage of the cleavable bismaleinimido derivatives used so far, which react with SH groups, is that the subsequent cleavage of the cross-linking reagents from the proteins must take place in acidic or alkaline media; these reaction conditions can cause a denaturation of the proteins, so that it is no longer possible to functionally detect them after the cleavage reaction. Moreover, undesired side reactions often occur during the cleavage reaction or during the acidic or alkaline hydrolysis.

The prior art bismaleinimido compounds can be considered to have the structure of formula IV

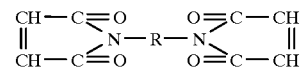

where R is the bridging radical which joins the heterocyclic rings and is generally either non-cleavable or is cleaved under relatively severe conditions.

According to Moore et al, op. cit., cross-linking of proteins with bis-maleimides can occur via the following mechanism.

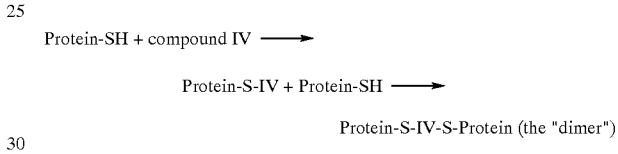

The greatly increased molecular weight of the "dimer" facilitates insolubilization and/or separation or removal of the protein from biological environments such as cells or from solubilizing media such as aqueous media. If the bridging radical R is, for example, an aromatic group, as in the case of N,N'-phenylene-bismaleimide, it is impractical to restore the protein to its original, non-cross-linked molecular weight. But even if the bridging radical is an ester group, as in the case of maleimidomethyl-3-maleimido propionate, the conditions for reasonably efficient alkaline hydrolysis (e.g. a pH of 13, as disclosed on page 1184 of Sato et al, op. cit.) can have undesirable effects.

According to the literature cited above, N-substituted maleimides (which can be N,N'-disubstituted and hence be bismaleic-imide-type compounds) can be prepared by the method of Searle, disclosed in U.S. Pat. No. 2,444,536, issued Jul. 6, 1948, wherein maleamic acid having hydrogen on the amido nitrogen is reacted with an anhydride of a saturated fatty acid (e.g. acetic anhydride) in the presence of an anhydrous alkali metal salt of a saturated fatty acid (e.g. sodium acetate). The method of preparation used by Sato et al, op. cit., is similar in principle; maleic anhydride is reacted with β-alanine and refluxed in the presence of acetic anhydride and sodium acetate to form an unbridged intermediate which reacts further to form the maleimidomethyl-3-maleimido propionate.

In view of the difficulties of restoring proteins bridged by bismaleic-imide-type reagents to their original (non-cross-linked) molecular weight, described above, there is still a need for cleavable cross-linking reagents which react with SH groups but which lack these disadvantages; for example, there is a need for cross-linking reagents which can form protein bridges, but the resulting protein can be cleaved under conditions sufficiently mild to substantially avoid protein denaturation. An objective of this invention is to provide such cross-lining reagents and a method for their preparation. A further objective is to provide a method for using these reagents and for obtaining proteins of decreased molecular weight from the resulting cross-linked product. Still another objective is to provide an analytical method for proteins solubilized in a medium or contained within a biological environment wherein the protein is first cross-linked to make it easier to characterize or remove or isolate, but the cross-links or bridges are then cleaved under mild conditions which essentially do not damage the protein.

SUMMARY OF THE INVENTION

This invention relates to, inter alia, dimaleinimido-substituted dihydroxyalkanes having the general formula I

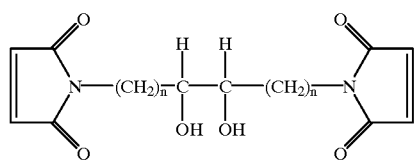
(I)

wherein n=1 to 6, preferably 1 or 2.

Optionally, the value of each "n" in formula I can be the same as or different from the other "n", but both "n" values are preferably the same.

Compounds of the formula I can be prepared in accordance with this invention by reacting a corresponding diaminoalkane diol, or an ammonium or diammonium salt thereof (e.g. a di-hydrohalide salt), with an N-substituted maleinimido derivative,. Examples of N-substituents on the N-substituted maleinimido derivative include groups such as —CO—OR', where R' is a substituted or unsubstituted aliphatic or aromatic (including heteroaliphatic or heteroaromatic) group.

The compounds of formula I can be used as a cleavable homobifunctional cross-linking agent for proteins. The resulting cross-linked product can be oxidatively cleaved with an oxidizing agent under mild conditions which will not have any substantial denaturing effect on proteins. For example, the conditions can include relatively short periods of time (e.g. less than an hour, typically 50 minutes or less), room temperature or ambient temperature conditions (15°30° C.), a pH value close to 7 (e.g. 5 to 9), and using an oxidizing agent which will not have any substantial denaturing effect on proteins, e.g. a peroxy compound such as a perhalogenate (preferably a periodate). The resulting oxidatively-cleaved product can have substantially the molecular weight of the starting protein, i.e. the molecular weight of the protein prior to cross-linking.

BRIEF DESCRIPTION OF THE DRAWING

In the accompanying Drawing,

FIG. 1 shows Western blots of protein, from bovine retinas, cross-linked by Na/Ca, K-exchangers and oxidatively cleaved (electrophoresis carried out in polyacrylamide gradient gel).

FIG. 2 shows a two-dimensional analysis in a polyacrylamide gel matrix illustrating the results of oxidative cleavage of protein bridging; in the first dimension of the analysis, molecular weight was determined by an immunoblot method, and in the second dimension of the analysis by an electrophoresis method.

DETAILED DESCRIPTION

The cross-linkers of this invention are believed to be distinguished by their relative ease of cleavage of the bridging radical which joins the maleinimido groups. This radical, which is has an alkyl chain substituted with adjacent hydroxyl groups, has the formula II

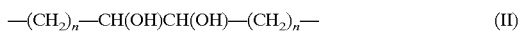
(II)

where n represents a number from 1 to 6, preferably 1 or 2, and each "n" can have the same or a different value, but the values of each "n" are preferably the same.

The bridging radical is introduced into the dimaleinimido-substituted cross-lining reagent by reacting the corresponding diaminoalkanediol or an ammonium (including diammonium) salt thereof with an N-substituted maleinimido derivative. Thus, the diamino or ammonium salt starting material has the formula III

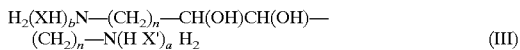
(III)

where X and X' are the anions of an acid, preferably a mineral acid such as a hydrohalic acid, a and b are zero or 1, and if a or b is 1, the corresponding nitrogen is positively charged, and n is as defined previously.

The preferred maleinimido derivatives are substituted on the ring nitrogen with (R"O)-carbonyl groups, where R" is alkyl, aryl, or hetaryl. Thus, the preferred N-substituted maleinimido derivatives are N-alkyoxycarbonyl, N-aryloxycarbonyl-, or N-hetaryloxycarbonyl-maleinimide.

Compounds of formula III are known; see, for example, Feit et al, J. Med. Chem. 10, 697 (1967), the disclosure of which is incorporated herein by reference. These compounds react at moderate temperatures (e.g. normal ambient temperatures) in polar liquid solvent media (e.g. aqueous media, which can include compatible organic polar solvents) with one of the N-substituted maleinimido derivatives; the diammonium salt compounds (where, in the compound of formula III, a and b=1 and each N is positively charged) are preferred and are preferably reacted in the presence of a proton acceptor or mildly basic agent such as an alkali metal carbonate or $NaHCO_3$. Suitable polar liquid organic solvents can, if desired, be aprotic, as in the case of aliphatic and cycloaliphatic ethers. The stoichiometry of the reaction medium is selected to favor the formation of the dimaleinimido compounds of this invention, e.g. at least about two moles of N-substituted maleinimido derivative are provided for each mole of compound III. A slight excess over stoichiometry (e.g. a 1 to 30% excess, preferably a 15 to 25% excess) is preferred to insure formation of the dimaleinimido product.

The resulting alkylenediol-bridged dimaleinimido compounds of this invention (the compounds of formula I, above) can be incubated with proteins in a manner well known in the art, e.g. at normal ambient temperatures or at moderately elevated temperatures for periods of time less than an hour.

Following the incubation of proteins with compounds of formula I, it became apparent that they were suitable as as homobifunctional cross-linking reagents. These reagents can be cleaved from the protein complex again after the cross-linking reaction; by means of an oxidate treatment, the cleavage reaction takes place under mild conditions and in a specific manner. The activity of the proteins is not influenced by the oxidative cleavage, so that the cleavability under the cited conditions also allows the analytical identification of the cross-linking components. Preferred oxidizing agents for the oxidative treatment are peroxy compounds such as the perhalogenates, e.g. alkali metal periodates, especially sodium periodate.

Bis-maleimides have been used for cross-linking polymers other than polypeptides; however, in other polymers it is often desirable that the cross-links be permanent. The principal advantages of this invention relate largely to the cross-linking of proteins wherein it is desirable to cleave the cross-links after the protein has been insolubilized or isolated or the like.

Thus, in conducting protein studies or analyses in accordance with principles of this invention, the protein—in a medium or environment such as antigens, antibodies, enzymes, biological membrane, blood, blood cells, endothelial tissue, or the like—can be cross-linked with compounds of formula I as a first step. The cross-linking greatly increases the molecular weight of the protein to be studied; for example, the molecular weight can be approximately doubled. To facilitate further study of the protein, its molecular weight can then be decreased (restored or recovered) to approximately its original amount, using the mild oxidative treatment described above. The resulting essentially non-cross-linked, essentially non-denatured protein of decreased molecular weight can be more easily or more accurately characterized or detected or isolated as compared to the cross-linked material.

The invention is further illustrated by the following non-limiting Examples.

EXAMPLE 1

Process for the preparation of D,L-dimaleinimido-2, 3-butane diol

One gram (12 mmol) of $NaHCO_3$ is cooled to 0° C. in a mixture consisting of 15 ml of tetrahydrofuran and 6 ml of water and then mixed under rapid agitation with 846 mg (3 mmol) of D,L-1,4-diamino-2,3-butane diol-dihydrobromide (P. W. Feit, O. T. Nielsen (1967), J. Med. Chem. 10, 697). The mixture is stirred for two minutes and subsequently 1.117 g (7.2 mmol) of N-methoxycarbonyl maleinimide is added portionwise. Afterwards, the mixture is stirred for three hours at room temperature, mixed with a small amount of water and extracted by shaking several times with acetic acid ethyl ester. The acetic acid ethyl ester extracts are lixiviated with water and NaCl solution, dried over $MgSO_4$ and reduced in a rotation evaporator. The D,L-1,4-dimaleinimido-2,3-butane diol, which precipitates as a colorless solid, is aspirated and washed with ether and pentane.

Yield: 164 mg (19.5% of the theoretical value) Melting range: 202° C. to 204° C. [395.6° F. to 399.2° F.] (degradation) $C_{12}H_{12}O_6N_2$ (280.24) calculated: C 51.43 H 4.32 N 10.0 found: C 51.64 H 4.51 N 9.63

EXAMPLES 2 AND 2A

Use of D,L-dimaleinimido-2,3-butane diol as a cleavable homobifunctional cross-linking reagent/ Comparison with phenylenemaleinimide crosslinkers Confirmation of Cross-linking and Comparison With Non-Cleavable Cross-linker The suitability of dimaleinimido-substituted dihydroxyalkane as a cross-linking reagent was confirmed with the example of the Na/Ca,K-exchanger of the vertebrate retina. After cross-linking with the SH-specific reagents p- and o-phenylenedimaleinimide, these proteins, having an apparent molar weight of 240 kD/mol, form non-cleavable cross-linking products having a molar weight of 490 kD/mol. Following reductive electrophoretic separation and electroelution, these products can be immunochemically detected on a protein-immobilizing membrane (PVDF membrane, Millipore) (P. J. Bauer (1995), Biophysical J. 68, A19).

Cleavable Cross-linking With Compound of Formula I

The same cross-linking product was also obtained after incubation in 50 $\mu$M D,L-1,4-dimaleinimido-2,3-butane diol for 10 minutes at room temperature. The cross-linking of the protein could be oxidatively cleaved within 20 minutes with 15 mM sodium periodate at room temperature and at a pH value of 7.5. After that, no more cross-linked product could be detected.

FIG. 1 correspondingly shows the substantiation of the cross-linking of Na/Ca,K-exchangers from bovine retinas with the dimaleinimido-substituted dihydroxyalkane and the oxidative cleavage after the action of sodium periodate. The substantiation is done by means of SDS-electrophoresis in 3.5% to 7.5%-polyacrylamide gradient gel with subsequent electroelution on a PVDF Immobilon Membrane (Millipore). The protein was immunochemically marked with the monoclonal antibody PMex2D9. The cross-linking was carried out in 100 $\mu$M D,L-1,4-dimaleinimido-2,3-butane diol. The following can be seen:

a: cross-linked protein without subsequent cleavage (a proteolytic degradation product is also marked at 1260 kD)

b: non-cross-linked sample c–h: cross-linked samples which had been oxidatively cleaved in different ways before the electrophoresis, namely, c: 50 minutes in 50 mM $NaIO_4$
d: 50 minutes in 30 mM $NaIO_4$
e: 50 minutes in 15 mM $NaIO_4$
f: 20 minutes in 50 mM $NaIO_4$
g: 20 minutes in 30 mM $NaIO_4$
h: 20 minutes in 15 mM $NaIO_4$ As shown in FIG. 2, the cross-linking product could also be oxidatively cleaved in polyacrylamide gel (3.5% to 7.5%) with 30 mM sodium periodate within 30 minutes at room temperature. Prior to this, protein cross-linking took place by means of incubation in 50 $\mu$M D,L-1,4-dimaleinimido-2,3-butane diol for 10 minutes. Subsequently, the sample was separated by means of SDS electrophoresis in 3.5% to 7.5% polyacrylamide gradient gel. The immunoblot with PMex2D9-marking is shown in FIG. 2 above ($1^{st}$ dimension). Prior to the oxidative cleavage, the solvent buffer tris(hydroxymethyl)aminomethane had to be replaced by triethanolamine, since tris(hydroxymethyl) aminomethane reacts with sodium periodate. A second gel trace was cut out and the solvent buffer was replaced by 20 mM triethanolamine-HCl at a pH of 7.5 and at room temperature (2-hour incubation). Subsequently, the bridging was cleaved with 30 mM sodium periodate at room temperature (30 minutes). The second SDS-electrophoresis ($2^{nd}$ dimension), in turn, likewise took place in 3.5% to 7.5% polyacrylamide gradient gel. The axes drawn in FIG. 2 shown the direction of ascending molar weight, whereby the molar weights 165 kD, 240 kD and 490 kD were plotted on both axes. Cleaved cross-linking products must occur below the diagonals drawn as dashed lines, while non-cleaved proteins come to lie on the diagonals. The immunoblot of this gel shows that, at 490 kD, no more cross-linking product can be detected and the oxidative cleavage led completely back to the 240 kD starting protein.

What is claimed is:

1. A dimaleinimido-substituted dihydroxyalkane having the general formula I

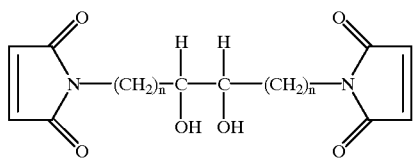

wherein n represents a number from 1 to 6.

2. A dimaleinimido-substituted dihydroxyalkane having the general formula according to claim 1, wherein n represents 1 or 2.

3. A dimaleinimido-substituted dihydroxyalkane having the general formula according to claim 1, wherein both n values of said general formula are the same.

4. A process for the preparation of dimaleinimido-substituted dihydroxyalkanes having the general formula I according to claim 1, comprising the step of reacting a corresponding diaminoalkane diol or an ammonium salt thereof with an N-substituted maleinimido derivative.

5. A process according to claim 4, comprising the step of reacting a di-ammonium salt of said diaminoalkane diol with the N-substituted derivative.

6. A process according to claim 4, wherein the N-substituted maleinimido derivative is N-alkoxycarbonyl-, N-aryloxycarbonyl-, N-hetaryloxycarbonyl-maleinimide or a combination thereof.

7. A method for cross-linking a protein, comprising the step of incubating the protein with a compound of the general formula I of claim 1.

8. A method for removing the cross-links of a protein which has been cross-linked with a compound of the general formula I of claim 1, comprising the step of oxidizing the thus-cross-linked protein with an oxidizing agent under essentially non-denaturing conditions.

9. A method according to claim 8, wherein said oxidizing step is carried out with a periodate as the oxidizing agent.

10. A method for cross-linking a protein and subsequently decreasing the molecular weight of the resulting cross-linked product, comprising the steps of:

cross-linking the protein with a compound of the general formula I of claim 1, and oxidatively cleaving the resulting cross-linked protein with an oxidizing agent under essentially non-denaturing conditions.

11. A method according to claim 10, wherein said cleaving step is carried out with a periodate as the oxidizing agent.

12. A method according to claim 10, wherein said method is an analytical method for improving the separability of a protein from an environment or medium and for essentially restoring its original, non-cross-linked molecular weight.

* * * * *